United States Patent [19]

McShane

[11] Patent Number: 5,230,428
[45] Date of Patent: Jul. 27, 1993

[54] APPARATUS FOR THE DISPOSAL OF CONTAMINATED NEEDLES

[76] Inventor: Jerry M. McShane, 2313 Killaraney, Deer Park, Tex. 77536

[21] Appl. No.: 766,822

[22] Filed: Sep. 26, 1991

Related U.S. Application Data

[63] Continuation-in-part of Ser. No. 538,926, Jun. 15, 1990, abandoned.

[51] Int. Cl.$^5$ .............................................. A61B 5/14
[52] U.S. Cl. .................................. 206/363; 206/364; 206/365; 604/192; 604/263
[58] Field of Search ................................ 206/363-370, 206/438; 604/192, 263

[56] References Cited

U.S. PATENT DOCUMENTS

| | | | |
|---|---|---|---|
| 3,416,657 | 12/1968 | Sorensen, Jr. et al. | 206/365 X |
| 3,637,072 | 1/1972 | Narvsawa et al. | 206/365 X |
| 4,248,246 | 2/1981 | Ikeda | 604/263 X |
| 4,742,910 | 5/1988 | Staebler | 206/365 |
| 4,845,923 | 7/1989 | Donovan | 206/364 X |
| 4,890,734 | 1/1990 | Gach | 206/366 |
| 4,936,449 | 6/1990 | Conard et al. | 206/366 |
| 5,038,929 | 8/1991 | Kubofcik | 206/366 X |

FOREIGN PATENT DOCUMENTS

| | | | |
|---|---|---|---|
| 645022 | 10/1928 | France | 604/192 |
| 92437 | 9/1968 | France | 206/365 |
| 292504 | 1/1932 | Italy | 206/366 |

*Primary Examiner*—Bryon P. Gehman
*Attorney, Agent, or Firm*—Pravel, Hewitt, Kimball & Krieger

[57] ABSTRACT

An apparatus and a method for the immediate elimination of hazards associated with exposure to biocontaminated needles. The apparatus includes a protective housing fabricated of a material that resists penetration by a needle and a resilient material capable of being easily penetrated by a needle but which offers substantial resistance to withdrawal of the needle.

9 Claims, 2 Drawing Sheets

FIG.8
FIG.9
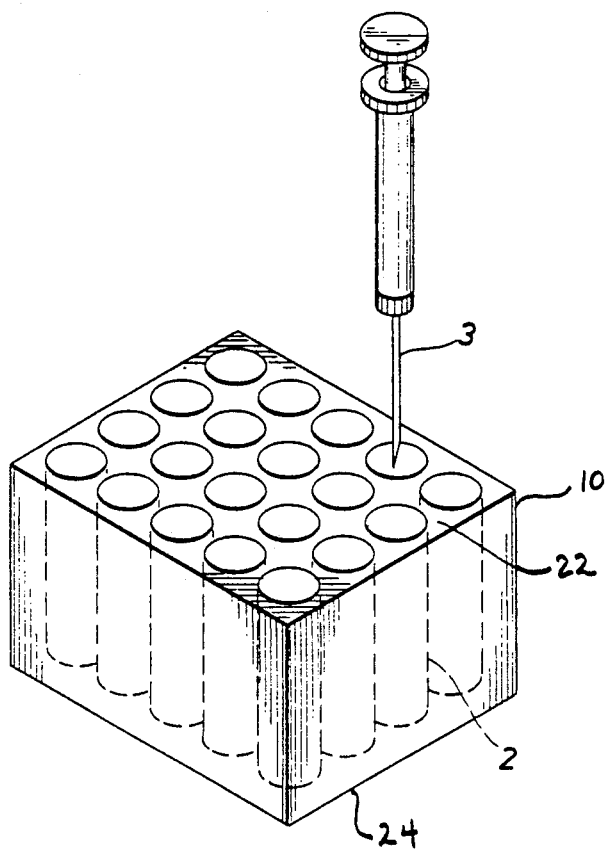
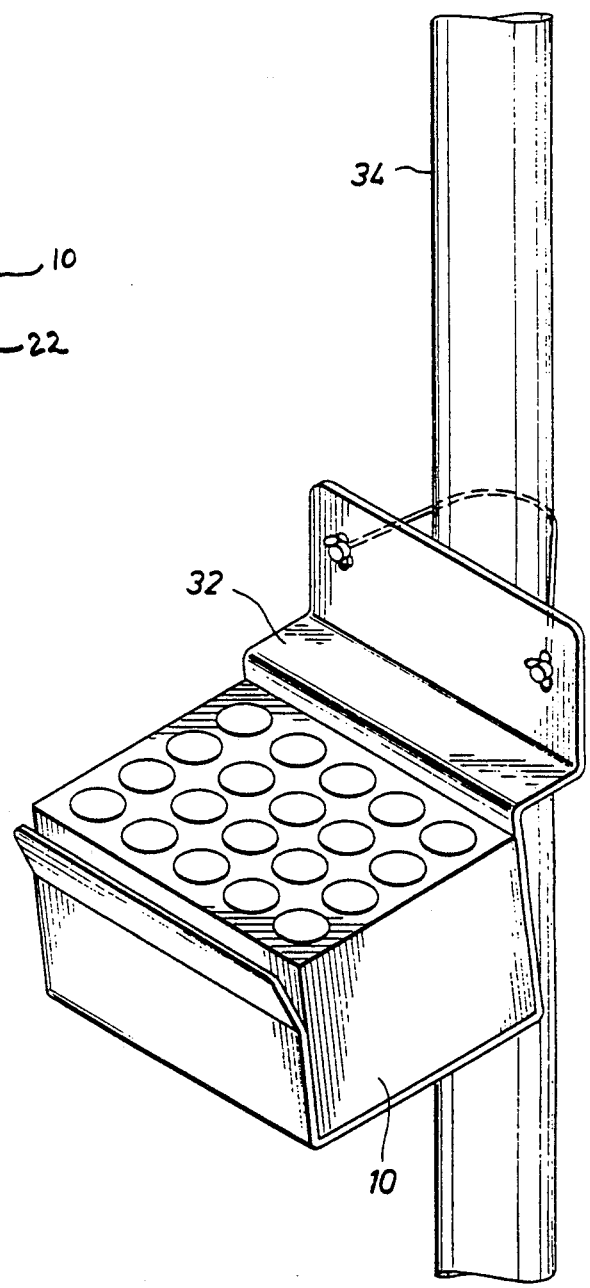

APPARATUS FOR THE DISPOSAL OF CONTAMINATED NEEDLES

This is a continuation-in-part of co-pending application Ser. No. 07/538,926 filed on Jun. 15, 1990, now abandoned.

FIELD OF THE INVENTION

This invention relates to an apparatus and method for reducing the hazards associated with contaminated syringe needles and other sharp objects and, more specifically, to an apparatus and method for the safe disposal of such sharp objects.

BACKGROUND OF THE INVENTION

Biologically contaminated needles present potential health risks to persons who come into contact with them, including the risk of exposure to HIV and hepatitis viruses. Accidental needle punctures and possible contamination of open wounds by exposed portions of used sharp objects such as syringe needles, catheters, and I.V. lines, present significant hazards to health care workers until they are safely disposed.

While needles generally include a protective cap (cannula) that is removed prior to use, the caps are generally fabricated of soft plastic and are of a small diameter. The health care worker may easily suffer an accidental needle puncture by missing the cannula opening with the needle. Reinsertion of the contaminated needle into the cannula may also result in the sharp needle penetrating the thin cannula wall and exposure of a health care Worker to the contaminated needle tip.

For these reasons, health and safety regulations generally forbid recapping of needles prior to their disposal because of the high incidence of injury and the possibility of contraction of infectious disease which may result from an attempt to replace the canula. OSHA Instruction 2-2.44A, dated Aug. 15, 1989, Office of Health Compliance Assistance states: "Needles shall not be recapped, purposely bent, or broken by hand, removed from disposal syringes, or otherwise manipulated by hand."

Special disposal containers have been developed for disposing of contaminated needles and other sharp items. Generally, these large containers are intended for repeated use and are placed near the site of use, for example on a shelf in an operating room, or in a hospital room. (See U.S. Pat. No. 4,736,844) Immediately after use, the sharp object, e.g. needle, remains unprotected until the contaminated needle is deposited in the container. Routine patient care as well as emergencies increase the risk of contact with an unprotected contaminated sharp object prior to its proper disposal.

Numerous devices have attempted to provide a safe and efficient means for protecting contaminated needles after use and prior to disposal. Most are complex, expensive, and inconvenient to use. Some include specially designed syringes and needle caps, but this requires that every needle come equipped with a special design; for example, hypodermic needles, I.V. needles, catheters, and the like. Some devices require precise fitting to the needle, and are limited to one specific size or type or design of needle.

One such device is shown in U.S. Pat. No. 4,848,569 where an apparatus is designed to protect the tips of contaminated needles. Blocks of a flexible material are used which can be penetrated by the tip of a needle. This device does not protect the entire needle and does not protect needles which may be inserted into the flexible material at an angle or which are long enough to protrude from the side of the block. For example, when a needle is inserted into rubber or other flexible material, the path of the needle through the flexible materials is generally not straight, but curved, generally in the direction away from the bevel of the needle. Even if the flexible blocks were large enough to cover the entire needle, the curved path of an inserted needle or insertion at an angle could result in the needle piercing a side wall of the flexible block, exposing health care workers to undesirable risk of harm.

In U.S. Pat. No. 4,845,923 a device is provided where a needle can be inserted into a disposal container and then contacted with one or more chemical agents to form a reaction product which immobilizes and encapsulates the contaminated object for disposal. The protection achieved by this device is not instantaneous, but requires time for the necessary chemical reactions to take place. This device is also complicated to use because it requires proper temperature and adequate mixing for activating the necessary chemical reactions.

Thus, there is a need for a simple, safe and effective device for the protection of health care workers from exposure to contaminated needles and other sharp objects, immediately after use and prior to disposal.

SUMMARY OF THE INVENTION

The apparatus of the present invention is believed to satisfy this need by providing a housing which covers the entire length of a needle and cannot be penetrated by the sharp object. An adherent plug is contained in the housing in which the contaminated sharp object can be inserted, and which adheres to the sharp object and prevents it from being dislodged or easily removed from the protective housing.

In a preferred embodiment, the apparatus includes an elongated protective housing formed of a glass tube, with adherent plug formed of a hot-melt adhesive at the open end of the tube. The housing is placed in a rack adapted to receive and selectively retain a plurality of housings.

The method of the present invention includes inserting a contaminated sharp object through an adherent plug and into a housing to cover the sharp object and virtually eliminate risk of exposure to health care workers. Immediately, or at a short time thereafter, the contaminated sharp object, e.g., needle, enclosed in a protective housing, may be safely disposed by lifting that portion of the object which protrudes from the plug and housing, e.g., the syringe, tubing or hub of an inserted needle, and thereby removing from the rack the entire housing-sharp object assembly and disposing the housed object in a proper disposal container.

BRIEF DESCRIPTION OF THE DRAWINGS

FIG. 8 is a perspective view of the invention in which a plurality of holders of the invention are mounted in a rack; and FIG. 9 is a perspective view of the rack of FIG. 8 mounted on an I.V. pole.

DETAILED DESCRIPTION OF PREFERRED EMBODIMENTS

Figure 1:
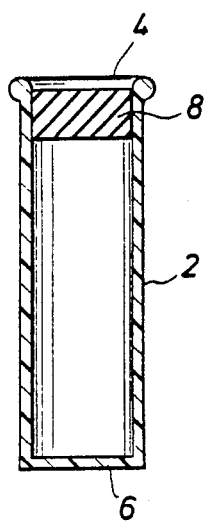
FIG. 1 is a sectional view of a housing in the form of an elongated tube of the present invention in which contaminated needles can be housed.
Figure 2:
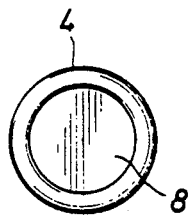
FIG. 2 is a top view of a tube of FIG. 1.

Referring to the FIGS. 1 and 2, an embodiment of the present invention is shown which includes an elongated protective housing 2, having a first open end 4 and a second closed end 6. A plug 8 is mounted in the open end 4 of the protective housing 2, which is adapted to receive a sharp object, e.g. a needle. The material of the plug 8 receives and retains an inserted sharp object immediately upon insertion, thereby preventing inadvertent dislodging of the object from its protective housing 2.

The protective housing 2 is fabricated of a material which prevents penetration by a sharp object, e.g., needle. Preferred materials include glass, metals, and hard plastics. More preferred is glass, such as, for example, a glass vial having a diameter of about 8 mm and a length of about 54 mm (Kimble Glass Co., Vineland, N.J.). The protective housing 2 may be of various shapes and sizes, but is preferably elongated, e.g., tubular.

The plug 8 can be formed of various solid, resilient materials including any elastomer capable of being easily penetrated by a needle by placing a load against the sharp object and along lines that extend between the side wall of the housing and the retained sharp object and that offers resistance to or prevents easy removal of an inserted sharp object. Examples of such elastomers include natural and synthetic rubber, cork, thermoplastic materials, and silicone rubber. Preferred materials include hot melt sealant, polyurethane sealant, polysulfide sealant, and acrylic adhesives. More preferred is a hot melt adhesive. Examples of such adhesives considered satisfactory for use in the present invention include Jet Melt ® adhesive (Number 764, the 3M Co., St. Paul, Minn.) and general purpose hot melt adhesive such as Craft All Purpose Hot Melt (Parker Group, Foxborough, Me.) and Eastobond M-5H Amorphous polyolefin (Eastman Chemical Products, Kingsport, Tenn.). Cork and rubber plugs are also particularly useful. Examples of rubber materials found to be most satisfactory for use in the present invention include rubbers having a hardness in the approximate range of 30-70 durometers.

The plug 8 may be varied in size, density, porosity, and other structural characteristics, with the proviso that the plug is capable of easily receiving and immediately retaining an inserted sharp object. The plug 8 must be fabricated of a material which permits easy penetration by the sharp end of a needle, without bending of the needle, and also immediately retains the needle and prevents the inserted needle from being inadvertently dislodged from the protective housing. The force required to withdraw an inserted needle from the plug material is substantially greater than the force developed by gravitational action in a separating direction on either the needle or the apparatus, i.e., when the other of the apparatus or needle is positively retained. The force required to withdraw an inserted needle from the plug material is also substantially greater than any centrifugal force developed by casual motion of the apparatus or the needle directed at separating the inserted needle and the apparatus. Casual motion would be that associated with ordinary and expected use of the apparatus in the method of needle disposal, including lifting, inverting, shaking, and rocking. The combination of frictional resistance and compressive action of the plug material prevents separation of the needle and apparatus by casual motion.

Figure 3:
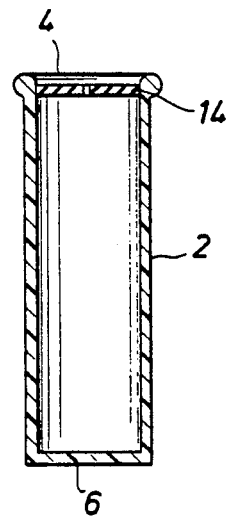
FIG. 3 is a sectional view of alternate embodiment of the invention.
Figure 4:
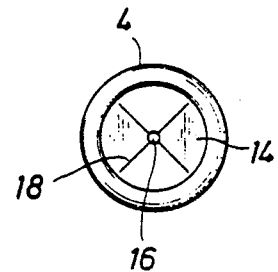
FIG. 4 is a top view of the embodiment of FIG. 3.

In an alternative embodiment, as shown in FIGS. 3 and 4, the plug 8 is a disc 14 which has a central aperture 16 radial slots 18 which allow for bending of the disc 14 to accept and retain an inserted needle. A needle penetrating the central aperture 16 causes the disc 14 to fold into the protective housing 2 and thereby hold the inserted needle. The disc 14 may be metal, for example stainless steel, spring steel, or a rigid plastic material capable of bending to accept the inserted sharp object, while at the same time affording the load required to resist or prevent retraction of the inserted needle. For example, a disc fabricated of spring steel prevents retraction of an inserted needle. A fastener, similar in design as those manufactured by Arden Fasteners No. PS062032PGS (Arden, Lavergne, Tenn.) may be useful as the disc 14 of the present invention. The disc 14 can be mounted in housing 2 by an appropriate adhesive, pressure fitted or clamped over the open end.

A plurality of protective housings 2 are preferably contained within a rack 10 adapted to receive the housings 2. The rack 10 may have many shapes and sizes and serve its function in containing the protective housings 2 of the invention. In the configuration illustrated in FIG. 8, the rack 10 is a rectangular block having a top 22 and a bottom 24. The rack 10 is adapted to receive and selectively retain a plurality of protective housings 2 through the top 22 of the rack 10.

The rack 10 may be fabricated of various materials including wood, vacuum formed plastics, metal, styrofoam and the like. The rack is designed to prevent the loss of the housings 2 from the rack 10 when inverted, but allows for easy removal of a housing 2 when adhered to a contaminated sharp object. The rack 10 may be adapted for mounting, for example by a fitted bracket 32, onto an I.V. pole 34 as shown in FIG. 9, a patient's bed, a phlebotomist's work tray, or other accessible location.

In the method of the invention, a biocontaminated sharp object, e.g., needle is inserted into a protective housing 2 through the plug 8 in the top of the housing 2, generally using only one hand, for example, while the housing is seated in a rack 10. After insertion, immediately or at a time thereafter, the entire needle housing assembly is removed by lifting the assembly out of the rack 10 and discarding the entirety in an appropriate biocontaminated waste container. The inserted needle is retained in this protective housing and is not easily dislodged during the transfer of the assembly to the waste container.

Figure 5:
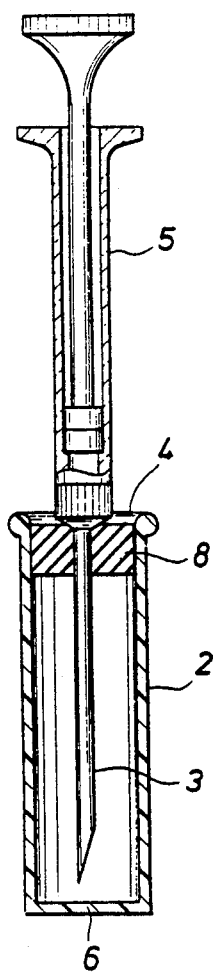
FIG. 5 is a sectional view of the embodiment of FIGS. 1 and 2 being used with a syringe.
Figure 6:
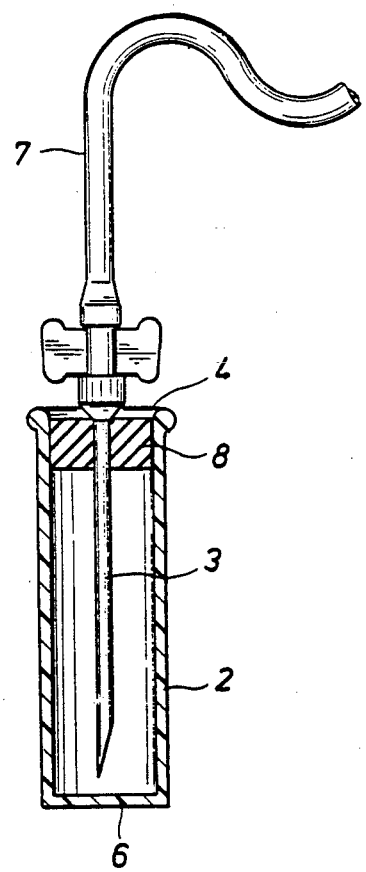
FIG. 6 is a sectional view of the embodiment of FIGS. 1 and 2 being used with an I.V. catheter.
Figure 7:
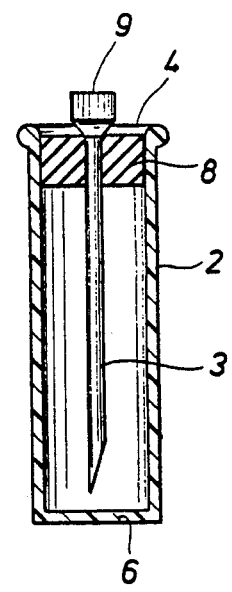
FIG. 7 is a sectional view of embodiment of FIGS. 1 and 2 being used with a detached needle.

As shown in FIGS. 5, 6, and 7, the apparatus of the present invention may be used for the disposal of biocontaminated sharp objects including needles attached to syringes, I.V. tubing, butterfly lines, and catheters, as well as free, unattached needles, lancets, scalpels, and scalpel blades. After insertion of the needle 3 into the adherent plug 8 of a protective housing 2, the entire assembly can be removed by lifting that portion attached to the sharp object 3 which protrudes out of the plug 8, for example, a syringe 5, tubing 7, or needle hub 9. The needle 3 is retained by the plug 8 thereby allowing the removal of the needle and its protective housing 2 simultaneously from the rack 10 for disposal in a proper biocontaminated waste container.

In a preferred embodiment, the housing may also include an antimicrobial agent, for example, an antiviral agent such as gluteraldehyde. The antimicrobial agent would contact the sharp object upon its insertion through the adherent plug thereby killing any microbes present on the sharp object.

The foregoing description is considered to be illustrative and not limiting and variations and improvements to the invention can be made without departing from the spirit and scope of the invention. All such variations and improvements are contemplated as falling within the scope of the appended claims.

We claim:

1. A system for disposing of an elongated biocontaminated sharp object that includes a distal sharp end portion, an elongated shaft, and a proximal end portion, comprising:

a protective housing having a closed end portion and a hollow interior communicating with an open end portion, the housing having a side wall portion fabricated of a material which prevents penetration by the sharp end portion of a said sharp object, the side wall defining an annular rim at the open end portion of the housing;

holding means contained in the housing, for receiving and retaining a sharp object, said means formed of a solid material with a centrally located opening that is receptive of a said sharp distal end portion of a said sharp object to retain a said sharp object;

said holding means comprising a rigid metallic disk positioned closely adjacent the annular rim so that a user can easily register a said sharp object into the holding means;

the disk having radial loading means for forming a load at the central opening against a said retained sharp object along radial lines that extend between a said retained sharp object and the side wall portion of the housing;

the said metallic disk comprising a plurality of radial slots that separate the disk into disk segments and which allows for bending of the disk during insertion of a retained sharp object; and wherein the radial loading means includes sufficient stiffness of the disk segments so that the segments bend to accept the sharp object while preventing removal of the said inserted sharp object.

2. The apparatus of claim 1, wherein the holding means includes a thin disc having a central aperture and at least two slots extending from the aperture for preventing removal of a needle after insertion of the needle through the aperture.

3. The apparatus of claim 1, wherein the disc is fabricated of stainless steel or spring steel.

4. A system for disposing of an elongated biocontaminated sharp object that includes a distal sharp end portion, an elongated shaft, and a proximal end portion, comprising:

a protective housing having a closed end portion and a hollow interior communicating with an open end portion, the housing having a side wall portion fabricated of a material which prevents penetration by the sharp end portion of a said sharp object, the side wall defining an annular rim at the end portion of the housing;

holding means contained in the housing, for receiving and retaining a said sharp object, said holding means formed of a solid, hard resilient material with a hardness of at least thirty (30) durometers that is easily penetratable by the sharp distal end portion of a said sharp object, but which offers substantial resistance to withdrawal of a said sharp object in order to retain the sharp object, the holding means being closely positioned adjacent the annular rim so that a user can easily register a said sharp object into the holding means;

said holding means further including radial loading means for forming a load against a said retained sharp object along radial lines that extend between the retained sharp object and the side wall portion of the housing;

and wherein the holding means will retain a said sharp object in the housing through a combination of frictional resistance against withdrawal of the retained sharp object and compressive action of the material on the retained sharp object, such that the force required to manually withdraw the retained sharp object from the holding means is greater than the gravitational and centrifugal force developed by casual motion of the housing and the retained sharp object.

5. The apparatus of claim 4, wherein the plug is fabricated of a natural of synthetic rubber, cork, or thermoplastic material, silicone rubber, or hot melt adhesive.

6. The apparatus of claim 1, wherein the holding ad retaining means is a plug located at the open end of the housing.

7. The apparatus of claim 1 or 4, wherein the housing is fabricated of metal.

8. The apparatus of claim 1 or 4, wherein the housing is fabricated of glass.

9. The apparatus of claim 1 or 4, further comprising an antimicrobial agent located in the housing.

* * * * *